United States Patent
Talebpour et al.

(10) Patent No.: US 11,339,366 B2
(45) Date of Patent: May 24, 2022

(54) METHODS OF PERFORMING NUCLEIC ACID STABILIZATION AND SEPARATION

(71) Applicant: QVELLA CORPORATION, Richmond Hill (CA)

(72) Inventors: Samad Talebpour, Richmond Hill (CA); Aye Aye Khine, Thornhill (CA)

(73) Assignee: QVELLA CORPORATION, Richmond Hill (CA)

( * ) Notice: Subject to any disclaimer, the term of this patent is extended or adjusted under 35 U.S.C. 154(b) by 277 days.

(21) Appl. No.: 16/347,658

(22) PCT Filed: Nov. 8, 2017

(86) PCT No.: PCT/CA2017/051329
§ 371 (c)(1),
(2) Date: May 6, 2019

(87) PCT Pub. No.: WO2018/085928
PCT Pub. Date: May 17, 2018

(65) Prior Publication Data
US 2019/0270961 A1 Sep. 5, 2019

Related U.S. Application Data

(60) Provisional application No. 62/419,340, filed on Nov. 8, 2016.

(51) Int. Cl.
| | | |
|---|---|---|
| *C12Q 1/68* | (2018.01) | |
| *C07H 21/00* | (2006.01) | |
| *C12N 1/06* | (2006.01) | |
| *C12N 15/10* | (2006.01) | |
| *C12Q 1/6806* | (2018.01) | |
| *C12Q 1/6809* | (2018.01) | |
| *C12Q 1/686* | (2018.01) | |
| *C12Q 1/6876* | (2018.01) | |

(52) U.S. Cl.
CPC ........... *C12N 1/06* (2013.01); *C12N 15/1003* (2013.01); *C12N 15/1017* (2013.01); *C12Q 1/6806* (2013.01); *C12Q 1/686* (2013.01); *C12Q 1/6809* (2013.01); *C12Q 1/6876* (2013.01); *C12Q 2527/101* (2013.01); *C12Q 2527/125* (2013.01); *C12Q 2561/113* (2013.01)

(58) Field of Classification Search
CPC .............................. C12Q 1/68; C12N 15/1003
See application file for complete search history.

(56) References Cited

U.S. PATENT DOCUMENTS

| | | |
|---|---|---|
| 5,010,183 A | 4/1991 | Macfarlane |
| 5,596,092 A | 1/1997 | Schneider |
| 5,728,822 A | 3/1998 | Macfarlane |
| 6,602,718 B1 | 8/2003 | Augello et al. |
| 6,617,170 B2 | 9/2003 | Augello et al. |
| 6,762,027 B2 | 7/2004 | Greenfield et al. |
| 7,303,876 B2 | 12/2007 | Greenfield et al. |
| 7,683,035 B1 | 3/2010 | Erbacher et al. |
| RE43,389 E | 5/2012 | Helftenbein |
| 2002/0063208 A1* | 5/2002 | Hastings ............ G01N 30/8624 250/281 |
| 2004/0014703 A1* | 1/2004 | Hollnder ................ C07C 211/64 514/44 R |
| 2005/0153292 A1 | 7/2005 | Stordeur et al. |
| 2009/0155769 A1* | 6/2009 | Niklasson ............... C12Q 1/701 435/5 |
| 2009/0208933 A1 | 8/2009 | Pachot et al. |
| 2011/0244467 A1* | 10/2011 | Haswell .............. B01L 3/50273 435/6.12 |
| 2013/0041145 A1 | 2/2013 | Kirsch et al. |

(Continued)

FOREIGN PATENT DOCUMENTS

| | | |
|---|---|---|
| EP | 0338591 A2 | 10/1989 |
| WO | 0214548 A1 | 2/2002 |

(Continued)

OTHER PUBLICATIONS del Pino et al., mRNA biomarker detection in liquid-based cytology: a new approach in the prevention of cervical cancer. Modern Pathology 28 :312 (Year: 2015).*

(Continued)

*Primary Examiner* — Ethan C Whisenant
(74) *Attorney, Agent, or Firm* — Hill & Schumacher

(57) ABSTRACT

Methods are provided for the stabilization and separation of nucleic acids from a sample via contact of the sample with a lysis and stabilization reagent that includes a cationic detergent. The cationic detergent lyses cells in the sample and stabilizes the released nucleic acids via the formation of nucleic acid-surfactant (NAS) complexes. The NAS complexes are centrifugally precipitated, washed, the resuspended in an aqueous resuspension liquid, forming a NAS complex suspension. The suspension is thermally processed to disintegrate the NAS complexes, thereby releasing the nucleic acids and forming a nucleic acid solution. In some example embodiments, the aqueous resuspension liquid is selected to be suitable for performing molecular amplification assays, such that the nucleic acid solution may be employed for performing a molecular amplification assay in the absence of further nucleic acid extraction. Examples are provided whereby the present methods are adapted for performing transcriptomic biomarker assays.

36 Claims, 14 Drawing Sheets

Specification includes a Sequence Listing.

(56) References Cited

U.S. PATENT DOCUMENTS

| | | | |
|---|---|---|---|
| 2013/0331298 A1* | 12/2013 | Rea | C12Q 1/6844 |
| | | | 506/16 |
| 2014/0199689 A1* | 7/2014 | Voss | C12N 15/1003 |
| | | | 435/6.1 |
| 2015/0093755 A1 | 4/2015 | Zhao et al. | |
| 2015/0225712 A1* | 8/2015 | Gunther | C12Q 1/6806 |
| | | | 506/9 |
| 2015/0259746 A1 | 9/2015 | Brandon et al. | |
| 2016/0068897 A1* | 3/2016 | Talebpour | C12Q 1/6806 |
| | | | 506/12 |
| 2016/0367981 A1* | 12/2016 | Wunderle | F16K 99/0034 |
| 2017/0073737 A1* | 3/2017 | Kempsell | C12Q 1/6883 |
| 2019/0270961 A1* | 9/2019 | Talebpour | C12N 15/1003 |
| 2020/0063208 A1* | 2/2020 | Zhang | C12Q 1/686 |

FOREIGN PATENT DOCUMENTS

| | | |
|---|---|---|
| WO | 2013013304 A1 | 1/2013 |
| WO | 2014082160 A1 | 6/2014 |

OTHER PUBLICATIONS

Devonshire et al., Application of next generation qPCR and sequencing platforms to mRNA biomarker analysis. Methods 59: 89-100 (Year: 2013).*

Foulkes et al., The CDKN2A (p16) gene and human cancer. Molecular Medicine 3(1) : 5-20 (Year: 1997).*

Miura et al., Splice isoforms as therapeutic targets for colorectal cancer. Carcinogenesis 33(12) :2311-2319 (Year: 2012).*

Tigst Demeke et al: "Influence of DNA extraction methods, PCR inhibitors and quantification methods on real-time PCR assay of biotechnology-derived traits", Analytical and Bioanalytical Chemistry, Springer, Berlin, DE, vol. 396, No. 6, Sep. 30, 2009 pp. 1977-1990.

Philippe Corbisier et al: "Toward Metrological Traceability for DNA Fragment Ratios in GM Quantification. 1. Effect of DNA Extraction Methods on the Quantitative Determination of Bt176 Corn by Real-Time PCR", Journal of Agricultural and Food Chemistry, vol. 55, No. 9, May 1, 2007; pp. 3249-3257.

Biron et al, "Bio markers for Sepsis: What Is and What Might Be?", Bio Insights 10, 7-17, (2015).

Feezoret al, "Whole blood and leukocyte RNA isolation for gene expression analyses", Physiol. Genom. 19, 247-254, (2004).

Macfarlane et al, "Isolating RNA from whole blood the dawn of RNA-based diagnosis?", Nature 362, 186-188 (1993).

McHugh et al, "A Molecular Host Response Assay to Discriminate Between Sepsis and Infection-Negative Systemic Inflammation in Critically Ill Patients: Discovery and Validation in Independent Cohorts", PLOS Medicine, DOI:10.1371/journal.pmed.1001916, 1-35 (2015).

Peronnet et al, "Evaluation of mRNA Biomarkers to Identify Risk of Hospital Acquired Infections in Children Admitted to Paediatric Intensive Care Unit", PLOS ONE DOI:10.1371/journal.pone.0152388, 1-13 (2016).

Ratzinger et al, "Utility of Sepsis Biomarkers and the Infection Probability Score to Discriminate Sepsis and Systemic Inflammatory Response Syndrome in Standard Care Patients", PLOS ONE 8, e82946-e82946 (2013).

Reinhart et al, "New Approaches to Sepsis: Molecular Diagnostics and Biomarkers", Clin. Micro. Rev. 25, 609-634 (2012).

Singer, "Biomarkers in sepsis", Curr. Opin. Pulm. Med. 19, 305-309 (2013).

Sutherland, "Development and validation of a novel molecular biomarker diagnostic test for the early detection of sepsis", Crit. Care 15, 1-15 (2011).

International Search Report PCT/CA2017/051329 dated Feb. 1, 2018.

B. Munaro, "Maize Seeds Sampling and DNA Extraction", Report on the Validation of a DNA Extraction Method from Maize Seeds, (Aug. 3, 2007), https://gmo-crl.jrc.ec.europa.eu/summaries/MIR604_DNAExtr.pdf.

* cited by examiner

| Storage time delay | 2 hours |
| --- | --- |
| Storage temperature | Room temperature |
| First sedimentation volume | 1mL mixture + 0 mL buffer |
| First sedimentation time | 3 min |
| Number of washes | 4 |
| NAS-complex disintegration | Heat, $T_d=95$, $t_d=10$ min |

FIG. 2A

| Storage time delay | 15 minutes to 3 days |
|---|---|
| Storage temperature | room temperature or Freezing temperature |
| First sedimentation volume | 1mL mixture + 9 mL buffer |
| First sedimentation time | 10 min |
| Number of washes | 3 |
| NAS-complex disintegration | Heat, $T_d=95$, $t_d=10$ min |

FIG. 3

| Experiments | GAPDH | | LAMP1 | |
|---|---|---|---|---|
| | RT-PCR | PCR | RT-PCR | PCR |
| Storage time delay at room temperature | | | | |
| 15 min | 27.73 | 31.28 | 29.17 | 33.33 |
| 1 hr | 27.34 | 31.23 | 25.49 | 33.74 |
| 2 hr | 28.08 | 31.53 | 25.48 | 33.50 |
| 3hr | 28.07 | 31.55 | 27.88 | 33.56 |
| 1 Day | 29.29 | 32.16 | 24.70 | 35.74 |
| 2 Days | 29.76 | 33.30 | 29.47 | 36.42 |
| 3 Days | 28.67 | 29.73 | 26.80 | 32.13 |
| | | | | |
| Frozen samples with storage time delay at room temperature | | | | |
| 1 hr | 26.77 | 31.42 | 26.11 | 33.84 |
| 3 hr | 28.66 | 32.27 | 26.86 | 33.99 |
| 5 hr | 28.85 | 32.01 | 27.47 | 34.85 |
| 1 Day | 29.56 | 32.25 | 26.63 | 33.21 |

FIG. 4

| | |
|---|---|
| Storage time delay | 15 minutes to 2 hours at room temperature |
| Storage temperature | room temperature<br><br>or<br><br>frozen temperature |
| First sedimentation volume | 1mL mixture + 0 mL buffer |
| First sedimentation time | 1 to 10 min |
| Number of washes | 4 |
| NAS-complex disintegration | Heat, $T_d$=95, $t_d$=10 min |

FIG. 5

| Experiments | GAPDH | | LAMP1 | |
|---|---|---|---|---|
| | RT-PCR | PCR | RT-PCR | PCR |
| Storage time delay of 15 minutes at room temperature | | | | |
| 1 min | 26.90 | 28.53 | 26.77 | 33.69 |
| 3 min | 27.36 | 29.84 | 27.76 | 33.83 |
| 5 min | 28.58 | 31.02 | 28.86 | 35.03 |
| 10 min | 27.82 | 30.24 | 28.16 | 33.10 |
| | | | | |
| Storage time delay of 2 hours at room temperature | | | | |
| 1 min | 27.46 | 30.54 | 27.57 | 34.59 |
| 3 min | 27.02 | 31.04 | 27.05 | 36.29 |
| 5 min | 26.19 | 29.80 | 27.19 | 36.05 |
| 10 min | 27.53 | 29.06 | 27.97 | 35.31 |
| | | | | |
| Immediately frozen samples, storage time delay of 1 hour at room temperature | | | | |
| 1 min | 26.35 | 29.74 | 25.71 | 37.93 |
| 3 min | 26.78 | 30.82 | 25.78 | N/D |
| 5 min | 27.87 | 30.10 | 26.76 | N/D |
| 10 min | 27.52 | 30.43 | 26.60 | N/D |
| | | | | |
| Frozen after 3 hr at RT, storage time delay of 1 hour at room temperature | | | | |
| 1 min | 27.03 | 29.44 | 25.53 | N/D |
| 3 min | 27.39 | 29.47 | 26.69 | 37.76 |
| 5 min | 27.23 | 29.56 | 26.04 | N/D |
| 10 min | 27.31 | 29.39 | 26.96 | N/D |

FIG. 6

| Storage time delay | 1 hour at room temperature |
| --- | --- |
| Storage temperature | Frozen immediately |
| First sedimentation | 1mL mixture + 0 mL buffer |
| First sedimentation time | 3 min |
| Number of washes | 4 |
| NAS-complex disintegration | Heat, $T_d$=35 to 95, $t_d$=10 min |

FIG. 7

| Experiments | GAPDH | | LAMP1 | |
|---|---|---|---|---|
| | RT-PCR | PCR | RT-PCR | PCR |
| 95°C | 26.47 | N/D | 24.69 | N/D |
| 85°C | 27.03 | 34.66 | 25.09 | N/D |
| 75°C | 28.54 | N/D | 28.13 | N/D |
| 65°C | 32.06 | N/D | 31.90 | N/D |
| 55°C | 33.83 | 33.58 | 33.90 | N/D |
| 45°C | N/D | N/D | 35.89 | N/D |
| 35°C | N/D | N/D | 36.12 | N/D |
| no treatment | N/D | N/D | N/D | N/D |

| Storage time delay | 1 hour at room temperature |
|---|---|
| Storage temperature | Frozen immediately |
| First sedimentation | 1mL mixture + 0 mL buffer |
| First sedimentation time | 3 min |
| Number of washes | 4 |
| NAS-complex disintegration | Heat, $T_d$= 95, $t_d$=1 to 10 min |

FIG. 9

| Experiments | GAPDH | | LAMP1 | |
|---|---|---|---|---|
| | RT-PCR | PCR | RT-PCR | PCR |
| 1 min | 27.19 | 33.33 | 26.33 | 35.88 |
| 3 min | 25.74 | 30.20 | 25.49 | 34.20 |
| 5 min | 25.71 | 30.74 | 25.46 | 33.37 |
| 10 min | 26.47 | 28.17 | 25.69 | 31.15 |
| no heat treatment | N/D | 36.95 | N/D | N/D |

FIG. 10

| | |
|---|---|
| Storage time delay | 1 hour at room temperature |
| Storage temperature | Frozen immediately |
| First sedimentation | 1mL mixture + 0 mL buffer |
| First sedimentation time | 3 min |
| Number of washes | 4 |
| NAS-complex disintegration | Heat, $T_d$= 95, $t_d$= 10 min<br><br>or<br><br>Flash heating |

FIG. 11

| Experiments | GAPDH | | LAMP1 | |
|---|---|---|---|---|
| | RT-PCR | PCR | RT-PCR | PCR |
| Heat treatment-1 | 28.00 | 30.02 | 30.36 | N/D |
| Flash heating - 1 | 28.28 | 33.28 | 31.48 | N/D |
| Heat treatment-2 | 27.27 | 29.99 | 28.61 | N/D |
| Flash heating-2 | 26.43 | 28.49 | 29.02 | 33.85 |

FIG. 12

| First sedimentation | 1mL mixture + 1 mL buffer |
|---|---|
| First sedimentation time | 3 min |
| Number of washes | 1,2,3,4 |
| NAS-complex disintegration | Heat, $T_d$= 95, $t_d$= 10 min |

FIG. 13

| Experiments | LAMP1 | |
|---|---|---|
| | RT-PCR | PCR |
| 1 wash | N/D | N/D |
| 2 washes | 32.78 | N/D |
| 3 washes | 28.57 | N/D |
| 4 washes | 28.07 | 37.73 |

FIG. 14

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: LAMP1 forward primer

<400> SEQUENCE: 1
accgtcctgc tcttccagtt                                               20

<210> SEQ ID NO 2
<211> LENGTH: 18
<212> TYPE: DNA
<213> ORGANISM: Artificial
<220> FEATURE:
<223> OTHER INFORMATION: LAMP1 reverse primer

<400> SEQUENCE: 2
ggcagggtct ctggcgtc                                                 18

<210> SEQ ID NO 3
<211> LENGTH: 19
<212> TYPE: DNA
<213> ORGANISM: Artificial
<220> FEATURE:
<223> OTHER INFORMATION: GAPDH forward primer

<400> SEQUENCE: 3
```

```
gccacatcgc tcagacacc                                          19

<210> SEQ ID NO 4
<211> LENGTH: 22
<212> TYPE: DNA
<213> ORGANISM: Artificial
<220> FEATURE:
<223> OTHER INFORMATION: GAPDH reverse primer

<400> SEQUENCE: 4
gttaaaagca gccctggtga cc                                      22
```

METHODS OF PERFORMING NUCLEIC ACID STABILIZATION AND SEPARATION

CROSS-REFERENCE TO RELATED APPLICATION

This application is a National Phase application claiming the benefit of the international PCT Patent Application No. PCT/CA2017/051329, filed on Nov. 8, 2017, in English, which claims priority to U.S. Provisional Application No. 62/419,340, titled "METHODS OF PERFORMING NUCLEIC ACID STABILIZATION AND SEPARATION" and filed on Nov. 8, 2016, the entire contents of which are incorporated herein by reference.

BACKGROUND

The present disclosure relates to methods of separating nucleic acids from samples. In some aspects, the present disclosure relates to methods of rapid transcriptomic profiling, including performing rapid mRNA biomarker assays on whole blood samples.

Cationic detergents (surfactants) have been known to be suitable as agents for the lysis of cells in a sample, and also for the stabilization of nucleic acids such as various forms of RNA. For example, in U.S. Pat. Nos. 5,010,183 and 5,728,822, Macfarlane teaches methods whereby cationic detergents, when mixed with a sample, effectively lyse cells within the sample, while forming a complex with nucleic acids released from the cells that stabilizes the nucleic acids and prevents gene induction. Unfortunately, the subsequent processing of such complexes for the release of nucleic acids, as taught in the art, requires complicated steps that involve nucleic acid extraction, which are not readily implemented in an automated system.

SUMMARY

Methods are provided for the stabilization and separation of nucleic acids from a sample via contact of the sample with a lysis and stabilization reagent that includes a cationic detergent. The cationic detergent lyses cells in the sample and stabilizes the released nucleic acids via the formation of nucleic acid-surfactant (NAS) complexes. The NAS complexes are centrifugally precipitated, washed, the resuspended in an aqueous resuspension liquid, forming a NAS complex suspension. The suspension is thermally processed to disintegrate the NAS complexes, thereby releasing the nucleic acids and forming a nucleic acid solution. In some example embodiments, the aqueous resuspension liquid is selected to be suitable for performing molecular amplification assays, such that the nucleic acid solution may be employed for performing a molecular amplification assay in the absence of further nucleic acid extraction. Examples are provided whereby the present methods are adapted for performing transcriptomic biomarker assays.

Accordingly, in a first aspect, there is provided a method of processing a sample to release nucleic acids therefrom, the method comprising:

forming a mixture comprising the sample and a lysis and stabilizing reagent, the lysis and stabilizing reagent comprising a cationic detergent, the cationic detergent being capable of lysing cells present in the sample and forming a complex with nucleic acids released from the cells, wherein the lysis and stabilizing reagent is provided in an amount sufficient to stabilize and prevent nucleic acid degradation;

separating the complex from the mixture;

resuspending the separated complex in an aqueous solution, thereby obtaining an aqueous suspension comprising the separated complex; and heating the aqueous suspension to a temperature above 50 degrees Celsius for a time duration suitable for dissociating the complex, thereby releasing the nucleic acids therefrom.

In another aspect, there is provided a method of a performing a molecular assay on a sample to detect nucleic acids released therefrom, the method comprising:

a) forming a mixture comprising the sample and a lysis and stabilizing reagent, the lysis and stabilizing reagent comprising a cationic detergent, the cationic detergent being capable of lysing cells present in the sample and forming a complex with nucleic acids released from the cells, wherein the lysis and stabilizing reagent is provided in an amount sufficient to stabilize and prevent nucleic acid degradation;

b) separating the complex from the mixture;

c) resuspending the separated complex in an aqueous solution, thereby obtaining an aqueous suspension comprising the separated complex;

d) heating the aqueous suspension to a temperature above 50 degrees Celsius for a time duration suitable for dissociating the complex, thereby forming a nucleic acid solution comprising the nucleic acids released from the complex; and e) performing an assay to detect nucleic acids present in the nucleic acid solution, wherein the assay is performed in absence of nucleic acid extraction.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 1C is a flow chart illustrating an example method of determining the transcriptomic profile of leukocytes for determining the status of a host's immune response to a microbial infection.

FIG. 2A is a table showing processing parameters pertaining to the results shown in FIGS. 2B-2E.

FIG. 3 is a table showing processing parameters pertaining to the results shown in FIG. 4.

FIG. 4 is a table showing biomarker and housekeeping gene assay results over a range of different storage conditions and times.

FIG. 5 is a table showing processing parameters pertaining to the results shown in FIG. 6.

FIG. 6 is a table showing biomarker and housekeeping gene assay results over a range of different storage conditions and times.

FIG. 7 is a table showing processing parameters pertaining to the results shown in FIG. 8A-8B.

FIG. 9 is a table showing processing parameters pertaining to the results shown in FIG. 10.

FIG. 10 is a table showing the dependence of the real-time RT-PCR assay cycle number on thermal incubation time at a temperature of 95° C.

FIG. 11 is a table showing processing parameters pertaining to the results shown in FIG. 12.

FIG. 12 is a table showing the effect of different heat treatment methods on RT-PCR assay cycle number.

FIG. 13 is a table showing processing parameters pertaining to the results shown in FIG. 14.

FIG. 14 is a table showing the effect of wash cycles on RT-PCR assay cycle number.

DETAILED DESCRIPTION

Figure 1A:
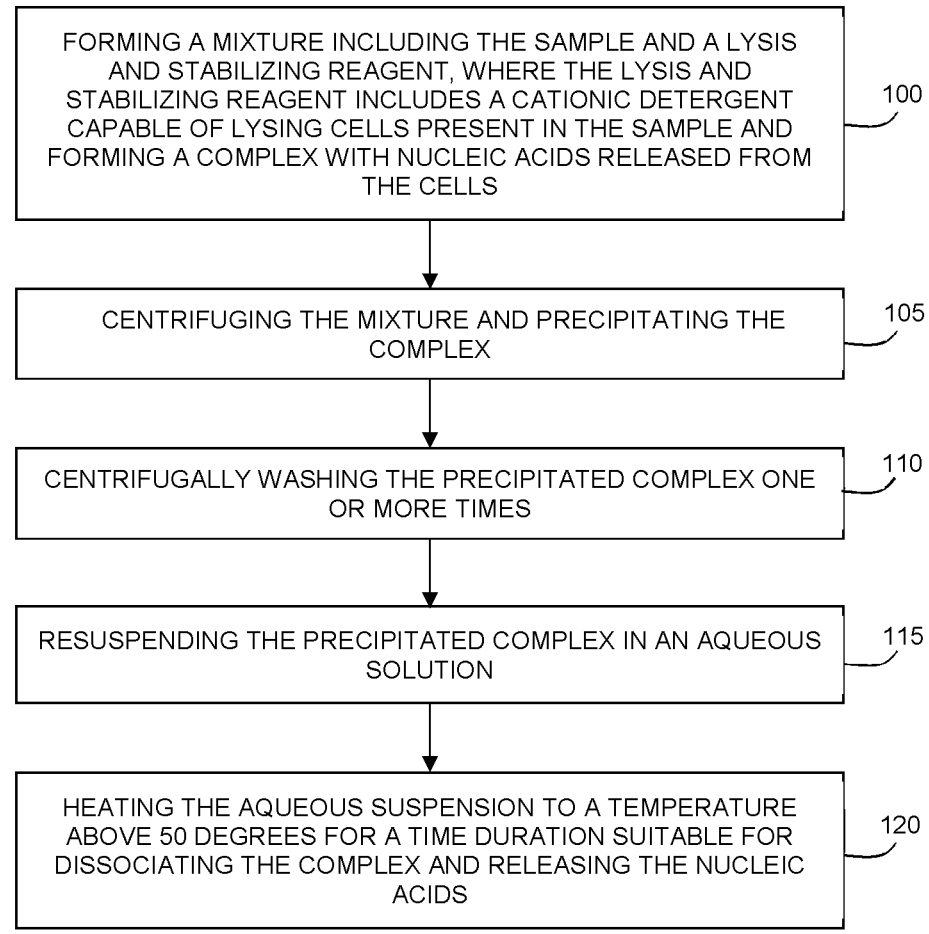
FIG. 1A is a flow chart illustrating an example method of processing a sample to separate nucleic acids using a cationic detergent.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein, the phrase "nucleic acid" refers to a single stranded or double stranded nucleic acid sequence that may consist of deoxyribonucleotides (DNA) or ribonucleotides (RNA), RNA/DNA hybrids or may be amplified cDNA or amplified genomic DNA, or a combination thereof.

Various example embodiments of the present disclosure relate to the use of cationic detergents during sample preparation. Cationic detergents (surfactants) have been known to be suitable as agents for the lysis of cells in a sample, and also for the stabilization of nucleic acids such as DNA and various forms of RNA (e.g. mRNA, tRNA, snRNA, lower molecular weight (LMW) RNA, rRNA and cRNA). For example, in U.S. Pat. Nos. 5,010,183 and 5,728,822, which are incorporated herein by reference in their entirety, Macfarlane teaches methods whereby cationic detergents, when mixed with a sample, effectively lyse cells within the sample, while forming a complex with nucleic acids released from the cells that stabilizes the nucleic acids and prevents gene induction.

Referring now to FIG. 1A, a flow chart is shown that illustrates an example implementation of stabilizing and separating nucleic acids from a sample. In step 100 of FIG. 1, a sample, such as a whole blood sample, is combined with a lysis and stabilization reagent that includes a cationic detergent (cationic surfactant) to form a mixture. The cationic detergent lyses cells within the sample and stabilizes the nucleic acids, forming a nucleic acid-surfactant (NAS) complex, as described above.

The mixture is then centrifuged in a centrifugation vessel such that the NAS complex is precipitated, as shown at step 105. The centrifugation is performed at a speed and time duration that are suitable for the pelleting of the precipitate. Non-limiting examples of centrifugation parameters are 100 g to 15,000 g for a time duration ranging from 1 to 20 minutes. After removal of the supernatant formed above the precipitate, the precipitate pellet is washed according to one or more wash cycles 110, each wash cycle involving the addition of a volume of an appropriate aqueous liquid to the centrifugation vessel, centrifuging the centrifugation vessel for a suitable time to re-pellet the complex, and removing the supernatant (or a substantial portion thereof). It has been found that a phosphate buffer (PB) having an ionic strength of 0.1 mM to 10 mM and pH 7.4, provides a suitable wash liquid, but it will be understood that other aqueous wash solutions may be used in the alternative, such as RNase free water.

Unlike the teachings in the art, such as those of Macfarlane, the present inventors have found that the nucleic acids bound to the NAS complex can be liberated, in a form that is suitable for downstream molecular assays, using a thermal processing step that causes disintegration (e.g. dissociation, disruption) of the complex.

Prior to the thermal disintegration step, the washed pellet is resuspended in an aqueous liquid. The aqueous liquid may be the same liquid as the aqueous wash liquid, or may be a different aqueous liquid. In one example implementation, the aqueous liquid is a phosphate buffer as described in the Examples below.

Having resuspended the NAS-complex in the aqueous liquid, the resulting suspension can be thermally processed to disintegrate the NAS complex and form a nucleic acid solution. This thermal disintegration step is shown at 120 in FIG. 1A. In one example embodiment, thermal disintegration may be performed by heating the NAS complex suspension above a pre-selected threshold temperature associated with disintegration, and maintaining the temperature of the suspension above the threshold temperature for a prescribed time duration. It will be understood that the thermal processing parameters for achieving NAS complex disintegration may vary depending on the type of cationic detergent that is employed.

In one example embodiment, the nucleic acid solution may be subjected to one or more centrifugation or filtration steps. For example, the nucleic acid solution may be centrifuged and the supernatant may be retained. Additionally or alternatively, the nucleic acid solution may be passed through a filter, and the filtrate may be collected.

The skilled artisan will be able to select a suitable temperature and time duration by performing a series of experiments at different thermal processing temperatures and thermal processing times, and measuring, directly or indirectly, the effect of the thermal processing conditions on the disintegration of the NAS complex. An indirect assessment of disintegration can be made, for example, by monitoring the quantity of nucleic acids recovered and amplified via a real-time reverse transcription assay, as described in the Examples below. A direct assessment of the disintegration of the NAS complex can be made, for example, by a detection modality that is sensitive to the presence of residual complexes that are not disintegrated, e.g. via optical absorbance or light scattering measurements.

For example, as shown below in the Examples, it has been found that for the case of samples processed via PAXgene™ tubes, disintegration of the complex occurs above a temperature of 50° C. when a thermal incubation time of 10 minutes is selected. However, further disintegration appears to occur as the temperature is increased, such that, for example, thermal processing temperatures exceeding 55° C., 60° C., 65° C., 70° C., 75° C., 80° C. may be preferred.

It will be understood that the thermal processing step described above may be implemented according to a wide variety of example implementations. In one example implementation, the resuspended NAS complex suspension may be disrupted by subjecting the complex to Joule heating via the generation of an internal electric current within the suspension.

For example, the rapid Joule heating method ("flash heating") disclosed in US Patent Application No. 2014/0004501, which is incorporated herein by reference in its entirety, may be employed to achieve thermal processing for achieving NAS-complex disintegration. This rapid Joule heating is performed by flowing the NAS-complex suspension into an electrical processing chamber having electrodes for the application of an electric field thereacross. The electrodes may be subjected to AC electrical voltage, such that the suspension is internally heated via Joule heating.

In one example embodiment, one or more of the electrodes may be blocking electrodes to prevent the formation of a Faradaic current in the suspension. The electrodes may be provided as a thin conductive substrate and with a thin dielectric coating in contact with the suspension within the electrical processing chamber, where the surface profile of the conductor and dielectric is microstructured for surface area enhancement such that the blocking electrode surface area substantially exceeds the surface area of the corresponding flat surface. The large capacitance thereby achieved enables a charging time greater than one microsecond, such as on the order of tens of microseconds. The capacitance of the blocking layer can also be enhanced by providing a thin dielectric layer having a high dielectric constant. In one example implementation, the metal substrate is aluminum, and the dielectric layer is aluminum oxide ($Al_2O_3$). This aluminum oxide ($Al_2O_3$) dielectric layer is formed by electrochemically oxidizing the aluminum (anodized aluminum). In order to increase the effective surface by as much as 100 times and to provide a corresponding increase to the capacitance per unit nominal area, the electrode is etched with a dense network of microscopic cavities and tunnels.

According to the present example implementation, the voltage may be applied such that the temperature of the suspension rises to, and optionally exceeds, 100° C. within a timescale of less than one second. The suspension may be superheated during thermal processing by regulating an internal pressure within the chamber.

According to the present example implementation, the aqueous resuspension liquid into which the NAS-complex is resuspended following the final washing step is selected to have a suitable ionic strength for generating Joule heating via the generation of ionic currents, and the electric field is provided with a sufficient frequency to support internal Joule currents and avoid substantial electric field screening effects. For example, the ionic strength of the aqueous resuspension liquid may be selected to be below a maximal value in order to support the establishment of an effective electric field with a suitable timescale for effecting electrical processing. The specific maximal value or range of suitable values of the ionic strength will mainly depend on the capability of the applied voltage source to deliver high voltage along with the corresponding current over the timescale over which the processing is desired to occur. It is to be understood that those skilled in the art may perform routine experimentation in order to determine a suitable upper limit or range of values for the ionic strength in a given application. According to other example implementations, the ionic strength of the aqueous resuspension liquid may range from approximately $0.1 \text{ mM} < I < 100 \text{ mM}$.

Without intending to be limited theory, it is presently contemplated that the disintegration efficiency of the present rapid Joule heating method may be dependent on the heating rate in order to effect rapid disintegration on thermal processing timescales of less than one second. Accordingly, in selected example embodiments, the heating rate of the suspension for the electrical processing may be greater than approximately 250° C./s, or greater than approximately 2000° C./s. Furthermore, without intending to be limited theory, it is presently contemplated that the disintegration efficiency of the present rapid Joule heating method may depend on the electric field that is applied within the suspension liquid during thermal processing in order to effect rapid disintegration on thermal processing timescales of less than one second. Accordingly, in selected example embodiments, voltages may be applied to the sample in order achieve internal electric fields ranging from 200 V/cm to 50 kV/cm, or 200 V/cm to 2 kV/cm, or 200 V/cm to 30 kV/cm, or 2 kV/cm to 50 kV/cm, or 2 kV/cm to 30 kV/cm.

As described above, the lysis and stabilizing reagent employed according to various example methods of the present disclosure includes a cationic detergent. The cationic reagent may be selected to be suitable for the lysis of a wide range of cells, including, but not limited to, erythrocytes, leukocytes, and microbial cells. In some example implementations, the lysis and stabilizing agent may be suitable for the lysis of viruses and the stabilization of viral nucleic acids. The nucleic acids may be present extra- and/or intracellularly in the biological sample.

It will be understood that the prior art teaches a wide range of suitable cationic detergent reagent formulations for effecting lysis and stabilization. In some example embodiments, the lysis and stabilizing reagent may include one or more cationic detergents, such as, not limited to, quaternary amine surfactants. Examples of suitable cationic reagents are disclosed by Macfarlane in U.S. Pat. Nos. 5,010,183 and 5,728,822 and by Augello et al. in U.S. Pat. No. 6,602,718.

The cationic detergent may be provided within a collection vessel, such as an evacuated collection tube, such as those disclosed by Augello et al. in U.S. Pat. No. 6,602,718, and such as the commercially available PAXgene™ collection tube (which contains<10% by weight of Tetradecyltrimethylammonium oxalate in an acidic solution (pH 3.7) of 2-4% Tartaric acid).

In some example embodiments, the lysis and stabilizing reagent may include one or more additional components, in addition to the cationic detergent. Nonlimiting examples of additional components include additional detergents, chaotropic salts, ribonuclease inhibitors, chelating agents and mixtures thereof.

It will be understood that although many of the example implementations described herein involve the processing of whole blood samples, it will be understood that the present disclosure is not intended to be limited to whole blood processing. For example, in some example implementations, the sample may be a blood containing sample that includes one or more types of blood cells. Non-limiting examples of biological samples other than whole blood include cell-containing compositions such as red blood cell concentrates, platelet concentrates, leukocyte concentrates, plasma, serum, urine, bone marrow aspirates, cerebral spinal fluid, tissue, cells, and other body fluids. The samples may be from human or animal origin, and the sample can be solid or liquid in nature (or a combination thereof). Solid samples may be processed by known pre-analytic methods, such as dissolving the solids in a suitable solution.

Although the preceding example method is described as employing centrifugation for the separation and washing of the NAS complex, it will be understood that the NAS complex may alternatively be separated via filtration.

Figure 1B:
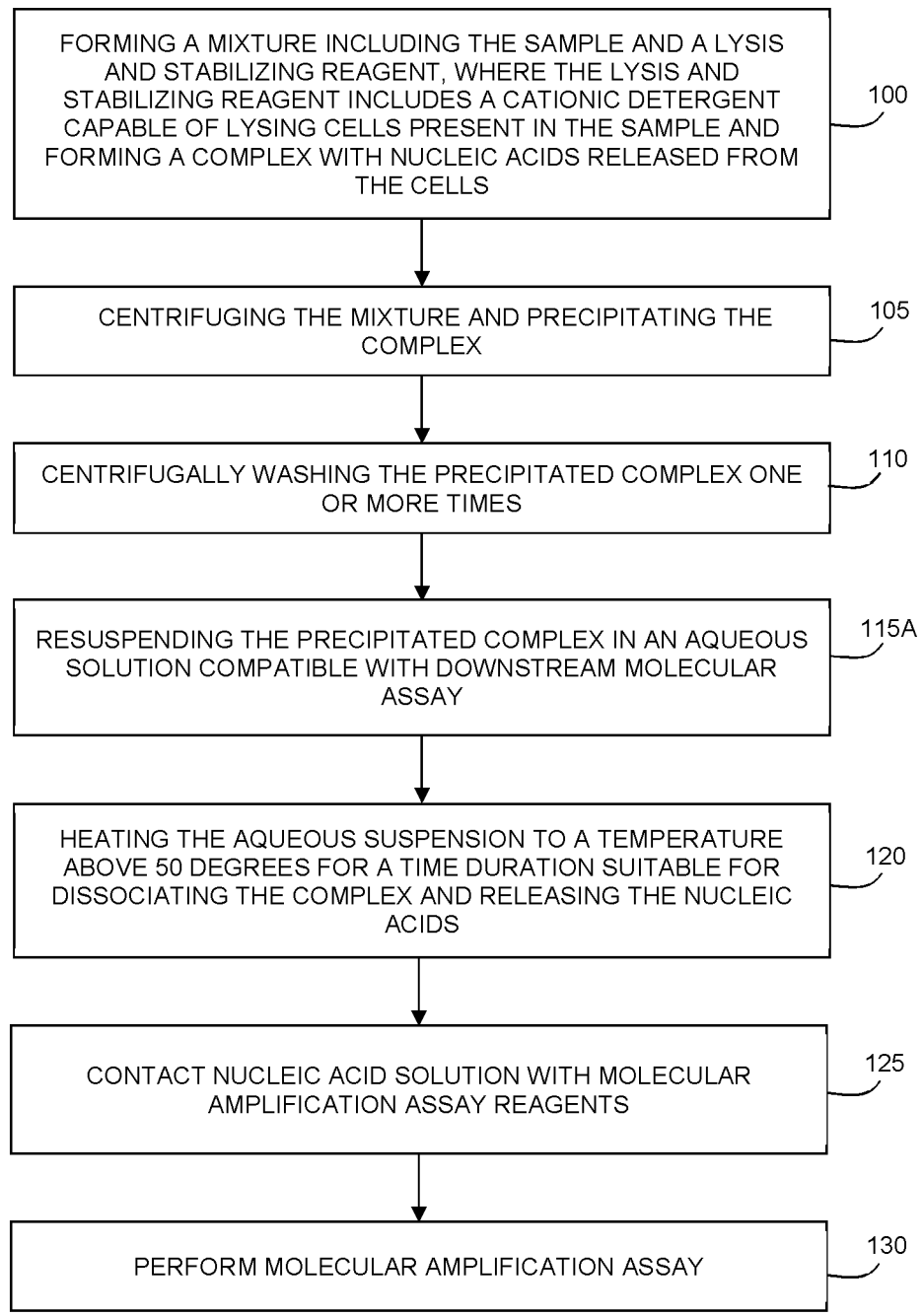
FIG. 1B is a flow chart illustrating an example method of processing a sample to separate nucleic acids using a cationic detergent, and subsequently performing a molecular assay in the absence of a nucleic acid extraction step.

Referring now to FIG. 1B, a flow chart is provided that illustrates an example implementation of a method of performing a molecular assay after thermal processing of the suspension and disintegration of the NAS complex, in the absence of an additional nucleic acid extraction step. As in FIG. 1A, the sample is treated by exposure to a lysis and stabilizing reagent, and the resulting NAS complexes are washed according to the centrifugal processing method described above. However, as shown in step 115A, the aqueous resuspension liquid (for resuspension of the NAS complex prior to thermal disintegration) is selected to be compatible with molecular amplification assays, such as, but not limited to, PCR, real-time PCR, reverse transcription PCR (RT-PCR) and real-time RT-PCT, such that when the nucleic acids are liberated via thermal disintegration, the resulting nucleic acid solution can be mixed with molecular amplification reagents without requiring an intermediate nucleic acid extraction step. This capability of the present method to perform nucleic acid separation in the absence of an intermediate nucleic acid extraction step may be beneficial when implementing the present methods on an automated platform.

After having dissociated the NAS complexes in step 120, the nucleic acid solution is contacted with assay reagents at step 125 for performing a molecular amplification assay. The assay is subsequently performed in step 130.

In one example embodiment, the nucleic acid solution may be subjected to one or more centrifugation or filtration steps prior to performing the assay. For example, the nucleic acid solution may be centrifuged and the supernatant may be retained. Additionally or alternatively, the nucleic acid solution may be passed through a filter, and the filtrate may be collected.

In some example implementations, the example method illustrated in FIG. 1B may be adapted to performing one or more transcriptomic biomarker assays. For example, the example method may be adapted to assess a partial transcriptomic profile of leukocytes based on a blood sample drawn from a subject. The example method may be employed to infer the state of subject's immune response to an infection, if present, such as a microbial infection.

In one illustrative example method, two gene sets are employed for determining a transcriptomic host response: an infection state indicator gene set (ISIG) comprising one or more transcriptomic biomarker genes, and a housekeeping gene set (HKG) comprising one or more nucleic acid housekeeping gene targets. The expression profile of HKG set is selected to not be significantly influenced by the health state of the host, while the expression profile of the ISIG set significantly changes if the host is infected by microbial cells.

In order to assess the host's state of health a volume of blood is drawn into an appropriate blood collection tube containing a cationic detergent. The cationic detergent lyses leukocytes in the sample and stabilizes mRNA from the leukocytes in the time interval between blood draw and the start of sample processing. Steps 100-120 of FIG. 1B are performed, yielding a nucleic acid solution ready for PCR and/or RT-PCR analysis. The resulting nucleic acid solution is assayed in spatially multiplexed real-time RT-PCR array and the relative level of each target mRNA from ISIG set is determined relative to its genomic DNA or relative to the level of at least one mRNA belonging to HKG set.

As described above, the nucleic acid solution obtained by performing step 120 is ready for proceeding with reverse transcription (RT) and polymerase chain reaction (PCR) assays for determining the average level of target mRNA in the original leukocytes. It will be understood that other assays that PCR may be employed to detect and/or quantify the mRNA, such as sequencing or other nucleic acid amplification assays.

In one example embodiment, the nucleic acid solution is split and is delivered into multiple reaction chambers and is mixed with reagents provided for performing reverse transcription and PCR. In one example embodiment, each chamber is provided with specific primers targeting the desired mRNA strand. Thus, in step 130, target mRNAs are converted to cDNA through the enzymatic reaction. During the subsequent thermal cycling, the cDNA and its corresponding DNA segment on the genomic DNA are amplified to amplicons.

In one example embodiment, the forward and reverse primers are designed such that the target section on the genomic DNA includes an intron segment. Thus, the amplicons originating from the mRNA and the genomic DNA will have different lengths and can be differentiated in step 130. In such a case, amplified mRNA and amplified genomic DNA can be separately identified, for example, by subjecting the amplicons to melting curve analysis.

In an alternative example embodiment, the reverse primer is designed to target one intron-exon junction (splice junction) region. This suppresses the conversion of pre-mRNA to cDNA during reverse transcription stage. Moreover, during PCR stage gDNA will have little contribution to the amplified product. In one example implementation, each reaction vessel may be provided with two pairs of reverse and forward primers; one pair for a gene from the ISIG set and another pair for a gene from the HKG set. The length of the cDNA are selected, through primer pair design, such that the melt peak corresponding to the two types of amplicons are sufficiently separated. Then, the transcriptomic level of the target gene will be determined by referencing the amplitude of its corresponding melt peak to the amplitude of the house keeping gene's melt peak.

EXAMPLES

The following examples are presented to enable those skilled in the art to understand and to practice embodiments of the present disclosure. They should not be considered as a limitation on the scope of the disclosure, but merely as being illustrative and representative thereof.

The examples described below illustrate non-limiting example implementations of some of the methods described above. In the forthcoming examples, 2.5 milliliters of whole blood was added to a PAXgene™ tube, forming a mixture in which nucleic acids from the leukocytes were stabilized as nucleic acid-surfactant complexes (NAS-complexes), and the mixture was stored at room temperature and processed after a storage time delay, tat, ranging from 15 minutes to 3 days. In some experiments, the mixture was frozen temperature and was processed after the storage time delay at room temperature for 1 hour to 1 day.

For the first sedimentation step, 1 mL of the mixture was added to a 0.8 mM pH 7.4 phosphate buffer (PB) with a volume $V_b$ ranging from 0 to 10 mL in a centrifuge tube, and centrifuged at 4000 g for a first sedimentation time, $t_{se}$, ranging from of 1 to 10 minutes. The supernatant was then removed and 100 μL of the residual liquid was left behind with the NAS-complex pellet in the tube.

Three to four cycles of washes were then performed, with each wash cycle being performed by adding 900 μL of PB buffer to the vessel, resuspending the pellet, centrifuging for 3 minutes at 4000 g, and removing 900 μL of the supernatant, such that a substantial volume of the supernatant liquid was removed. After the final wash, the NAS-complex was resuspended in the remaining approximately 100 μL of residual liquid.

The resulting suspension was subjected to a NAS-complex disintegration step by heat treatment at temperature $T_d$ for a period of $t_d$ minutes, thereby generating a nucleic acid solution. Both $T_d$ and $t_d$ were varied experimentally as shown in the examples presented below.

The resulting nucleic acid solution was passed through a filter with 0.45 μm pore size to remove residual complexes. One μL of the nucleic acid solution was then added to 1 μL of specific primer set (0.25 μM) and 3 μL of the respective mastermix and was subjected to a real-time RT-PCR or PCR assay. The example primer pairs that were employed in the present examples respectively target one infection state indicator gene (belonging to ISIG), lysosomal associated membrane protein 1 (LAMP1), and one housekeeping gene set (belonging to HKG), Glyceraldehyde 3-phosphate dehydrogenase (GAPDH).

The LAMP1 detection primers used in the following examples were forward (5'-ACCGTCCTGCTCTTCCAGTT-3') (SEQ ID NO 1) and reverse (5'-GGCAGGGTCTCTGGCGTC-3') (SEQ. ID NO. 2). The GAPDH detection primers used in the following examples were forward (5'-GCCACATCGCTCA-GACACC-3') (SEQ. ID NO. 3) and reverse (5'-GTTAAAAGCAGCCCTGGTGACC-3') (SEQ. ID NO. 4).

The RT-PCR mastermix included Taq polymerase and reverse transcriptase enzymes in appropriate buffer and used SYBR Green dye for signal detection. When performing the real-time PCR assay, the reverse transcription enzyme was not included in the mastermix. The assay signal was analyzed and two parameters were found: the threshold cycle, $C_T$, and the derivative melt peak ($\Delta T_m$).

Figure 2B:
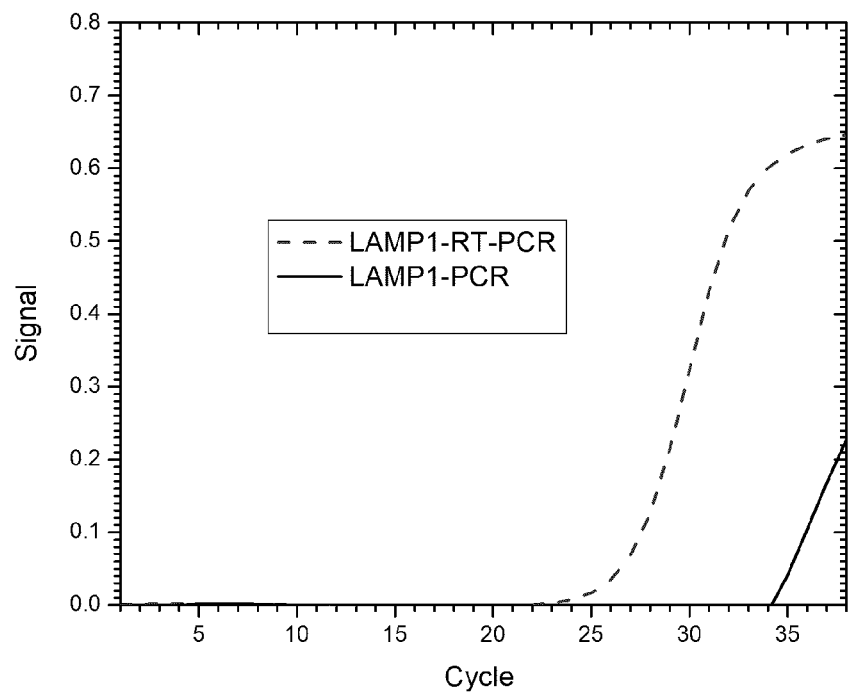
FIG. 2B plots the real time reverse transcription PCR (real-time RT-PCR) and real-time PCR signals of lysosomal associated membrane protein 1 (LAMP1) mRNA and genomic DNA detection obtained by processing a whole blood sample.
Figure 2C:
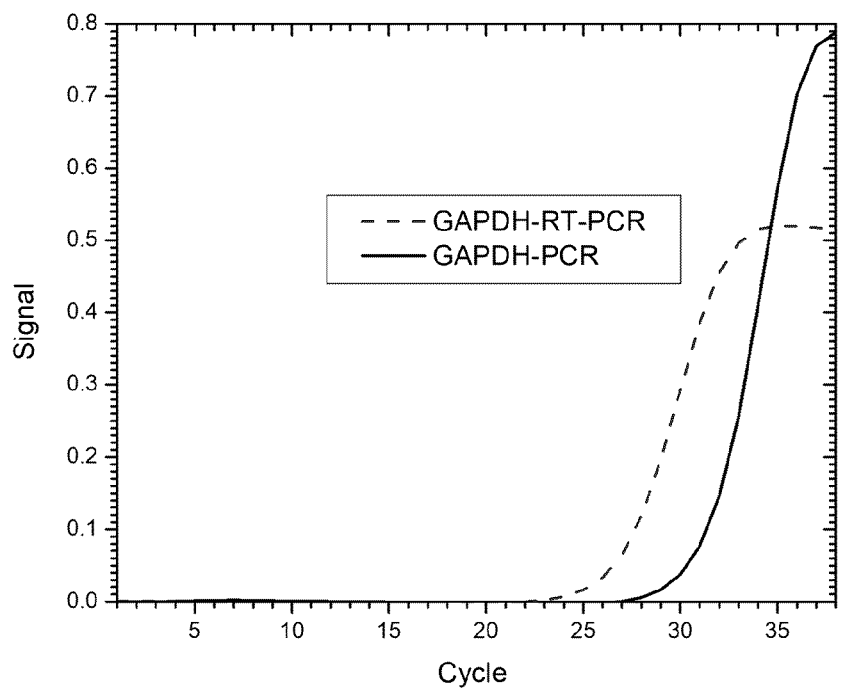
FIG. 2C plots the real time reverse transcription PCR (real-time RT-PCR) and real-time PCR signals of Glyceraldehyde 3-phosphate dehydrogenase (GAPDH) mRNA and genomic DNA detection obtained by processing a whole blood sample.
Figure 2D:
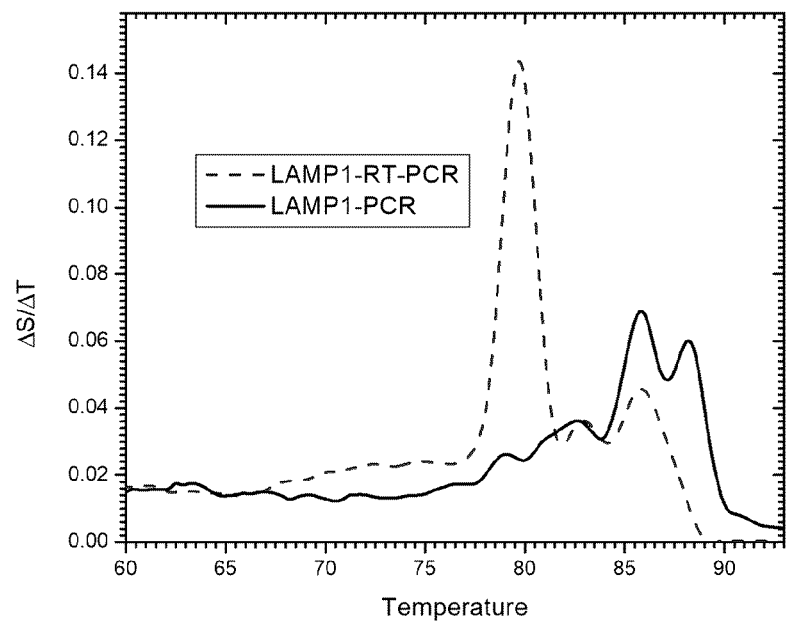
FIG. 2D plots the melting peaks of the amplicons at the end of the real-time RT-PCR and real-time PCR of FIG. 2A.
Figure 2E:
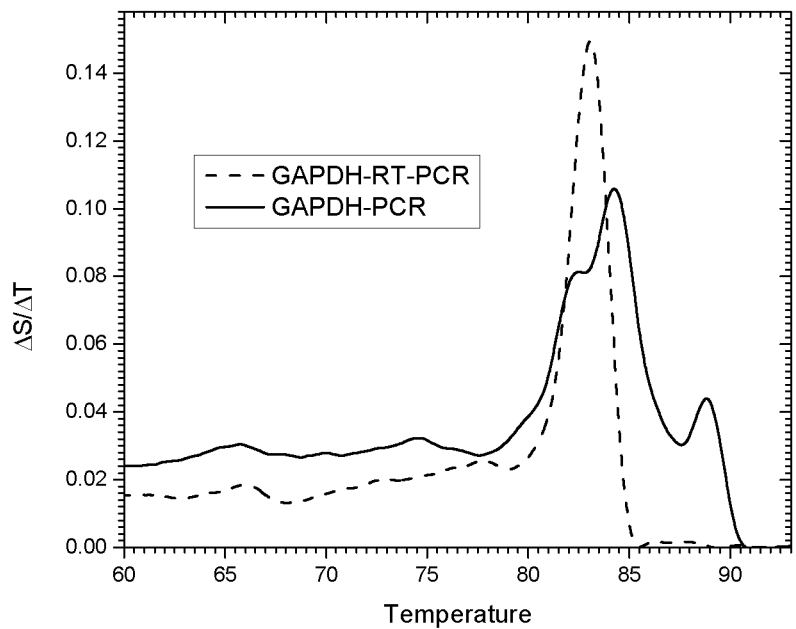
FIG. 2E plots the melting peaks of the amplicons at the end of the real-time RT-PCR and real-time PCR of FIG. 2B.

Example 1: Demonstration Transcription Profiling Using Method Involving Two Selected Genes The present example demonstrates the ability of an implementation of the aforementioned methods to detect mRNA along with its corresponding gDNA in a single reaction well, while differentiating their contribution to the amplified product by interrogating melt peaks. One mL of a sample/cationic detergent mixture from a PAXgene™ tube was processed with the parameters presented in FIG. 2A. Two amplification assays were performed in separate wells; a RT-PCR assay and a PCR only assay. The resulting amplification curves are presented in FIGS. 2B and 2C. The position of peaks in the corresponding derivative melt curves of FIGS. 2D and 2E indicate that aforementioned methods involving the use of heat to liberate nucleic acids from the NAS-complex are suitable for the detection and differentiation of mRNA and its corresponding gDNA.

Example 2: Processing of Sample/Cationic Detergent Mixture at Various Storage Time Delays and Storage Temperatures The present example is provided to demonstrate the robustness of the cationic detergent and sample mixture in the context of varying storage temperature and storage time. The processing parameters are presented in FIG. 3. The assay results of FIG. 4 indicate that the mixture can be stored in room temperature for times durations exceeding 3 days without compromising the ability to detect mRNA level in leukocytes using the example methods disclosed herein. Moreover, the results shown in FIG. 4 demonstrate that the mixture can be frozen for various time intervals without substantially affecting assay performance.

Example 3: Processing of Sample/Cationic Detergent Mixture at Different First Sedimentation Times The present example is provided to demonstrate that the NAS-complex is readily sedimented regardless of the storage condition. The processing parameters are presented in FIG. 5 and the assay results are presented in FIG. 6.

Figures 8A, 8B:
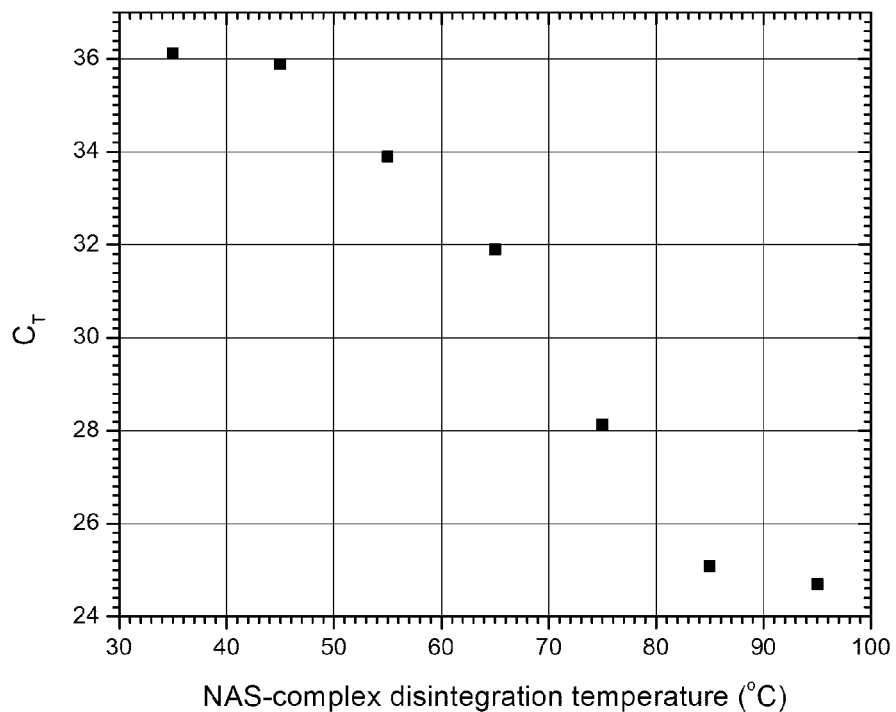
FIG. 8A is a table showing the dependence of nucleic acid-surfactant complex disintegration on temperature as evidenced by the real-time RT-PCR assay cycle number.
FIG. 8B plots the dependence of nucleic acid-surfactant complex (NAS-complex) disintegration on the processing temperature as evidenced by the real-time RT-PCR assay cycle number.

Example 4: Processing of Sample/Cationic Detergent Mixture Followed by Heat Treatment at Different Temperatures The present example is provided to investigate of the temperature, $T_d$, at which the NAS-complex disintegration is accomplished. The processing parameters are presented in FIG. 7. The results, which are presented in FIG. 8A, are also plotted in FIG. 8B. As it is observed in the figures, a processing temperature $T_d$ below 80° C. the results in higher real-time RT-PCR and real-time PCR cycle numbers, indicating a clear temperature dependence. Without intending to be limited by theory, it is believed that this assay result temperature dependence corresponds to a temperature dependence of disintegration (e.g. dissociation, disruption) of the NAS-complex.

Example 5: Processing of Sample/Cationic Detergent Mixture Followed by Heat Treatment at $T_d=95$ for Different Thermal Processing Times The present example is provided to demonstrate the dependence of the mRNA detection performance of an example implementation of the preceding method on the heat induced NAS-complex disintegration time. The processing parameters are presented in FIG. 9. The results, which are presented in FIG. 10, indicate that subjecting the washed NAS-complex to sufficiently high temperature for a period over 1 minute is sufficient to accomplish mRNA detection. Without intending to be limited by theory, it is expected that even shorter thermal processing times may be achievable at higher processing temperatures, and/or in the presence of a rapid rate of increase in temperature during heating.

Example 6: Processing of Sample/Cationic Detergent Mixture Followed by Heat Treatment or Flash-Heating Treatment The present example demonstrates the possibility of employing rapid Joule heating ("flash-heating") based thermal processing for achieving NAS-complex disintegration. In the current example, the NAS-complex suspension was introduced into an electrical processing chamber having a pair of electrodes for generating internal Joule heating. The electrical processing chamber had a volume of 20 μL and a thickness of 200 μm, with top and bottom electrodes. The electrodes were formed from microstructured aluminum with a conformal aluminum oxide dielectric layer, as described above. The NAS-complex was resuspended, after the final wash step, in PB buffer having an ionic strength of 0.8 mM. Electrical excitation was provided in the form of a series of square wave AC pulses of duration 50 μs and amplitude of 200 V, where the pulses were applied to the chamber for a duration 50 ms. It is believed that the temperature within the chamber exceeded 100° C. and that the heating rate exceeded 1500° C./s. The processing parameters are presented in FIG. 11. The assay results of FIG. 12 indicate that rapid Joule heating is similar to conventional heating in terms of the NAS-complex disintegration efficiency, while achieving NAS-complex disintegration on a much faster timescale.

Example 7: Dependence of RT-PCR Signal on Number of Washes

The present example demonstrates the effect of additional centrifugal wash cycles on the detection of an mRNA target via real-time RT-PCR. The processing parameters are presented in FIG. 13 and the assay results are presented in FIG. 14. The results demonstrate that in the present case, at least two wash cycles were necessary to detecting mRNA target via RT-PCR assay with a PCR cycle number of less than 30.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of processing a sample to release nucleic acids therefrom, the method comprising:
   forming a mixture comprising the sample and a lysis and stabilizing reagent, the lysis and stabilizing reagent comprising a cationic detergent, the cationic detergent being capable of lysing cells present in the sample and forming a complex with nucleic acids released from the cells, wherein the lysis and stabilizing reagent is provided in an amount sufficient to stabilize and prevent nucleic acid degradation;
   separating the complex from the mixture;
   resuspending the separated complex in an aqueous solution, thereby obtaining an aqueous suspension comprising the separated complex; and
   heating the aqueous suspension to a temperature above 50 degrees Celsius for a time duration suitable for dissociating the complex, thereby releasing the nucleic acids therefrom.

2. The method according to claim 1 wherein the aqueous suspension is heated above at least 70 degrees Celsius.

3. The method according to claim 1 wherein the aqueous suspension is heated above at least 80 degrees Celsius.

4. The method according to claim 1 wherein the aqueous suspension is heated for at least one minute.

5. The method according to claim 1 wherein the aqueous suspension is heated by Joule heating through an electric current applied thereto.

6. The method according to claim 1 wherein the sample is a blood containing sample.

7. The method according to claim 1 wherein the sample is a whole blood sample.

8. The method according to claim 7 wherein the whole blood sample is sampled directly into a blood collection vessel containing the lysis and stabilizing reagent.

9. The method according to claim 8 wherein the blood collection vessel contains less than 10% by weight of Tetradecyltrimethylammonium oxalate in an acidic solution (pH 3.7) of 2-4% Tartaric acid.

10. The method according to claim 1 wherein the complex is separated centrifugally by:
    centrifuging the mixture and precipitating the complex, thereby obtaining a precipitated complex;
    centrifugally washing the precipitated complex one or more times.

11. The method according to claim 1 wherein the complex is separated by filtration.

12. The method according to claim 7 wherein the complex is separated centrifugally by:
    centrifuging the mixture and precipitating the complex, thereby obtaining a precipitated complex;
    centrifugally washing the precipitated complex two or more times.

13. A method of a performing a molecular assay on a sample to detect nucleic acids released therefrom, the method comprising:
    a) forming a mixture comprising the sample and a lysis and stabilizing reagent, the lysis and stabilizing reagent comprising a cationic detergent, the cationic detergent being capable of lysing cells present in the sample and forming a complex with nucleic acids released from the cells, wherein the lysis and stabilizing reagent is provided in an amount sufficient to stabilize and prevent nucleic acid degradation;
    b) separating the complex from the mixture;
    c) resuspending the separated complex in an aqueous solution, thereby obtaining an aqueous suspension comprising the separated complex;
    d) heating the aqueous suspension to a temperature above 50 degrees Celsius for a time duration suitable for dissociating the complex, thereby forming a nucleic acid solution comprising the nucleic acids released from the complex; and
    e) performing an assay to detect nucleic acids present in the nucleic acid solution, wherein the assay is performed in absence of nucleic acid extraction.

14. The method according to claim 13 wherein the assay is a biomarker assay performed by contacting at least a portion of the nucleic acid solution with assay reagents comprising a primer set configured to detect a biomarker.

15. The method according to claim 14 wherein the biomarker is a messenger RNA biomarker.

16. The method according to claim 15 wherein the messenger RNA biomarker is associated with a genomic region comprising at least a portion of an intron.

17. The method according to claim 14 wherein the biomarker is associated with the response of a host to an infection.

18. The method according to claim 17 wherein the assay reagent are first assay reagents, and the primer set is a first primer set, the method further comprising:
    performing a housekeeping gene assay by contacting at least a portion of the nucleic acid solution with second assay reagents comprising a second primer set configured to detect housekeeping messenger RNA associated with a housekeeping gene;
    wherein the biomarker assay generates a biomarker reverse transcription assay result quantifying an amount of the biomarker present in the nucleic acid solution, and the housekeeping gene assay generates a housekeeping assay result quantifying an amount of the housekeeping messenger RNA present in the nucleic acid solution.

19. The method according to claim 18 further calculating a comparative measure comparing the biomarker reverse transcription assay result to the housekeeping gene reverse transcription assay result.

20. The method according to claim 19 wherein further comprising performing steps a) to e) one or more additional times on samples obtained at different time points; and
processing the comparative measures associated with the different time points to infer a time-dependent host response.

21. The method according to claim 17 wherein the primer set is a first primer set, and wherein the assay reagents further comprise a second primer set configured to detect genomic DNA associated with a selected gene, wherein the assay generates a biomarker reverse transcription assay result quantifying an amount of the biomarker present in the nucleic acid solution and a genomic DNA assay result quantifying an amount of the genomic DNA present in the nucleic acid solution, and wherein signals respectively associated with products amplified by the first primer set and the second primer set are distinguished via melt curve analysis.

22. The method according to claim 21 wherein at least a portion of the selected gene comprises at least a portion of an intron.

23. The method according to claim 21 further calculating a comparative measure comparing the biomarker reverse transcription assay result to the genomic DNA assay result.

24. The method according to claim 21 further comprising performing steps a) to e) one or more additional times on samples obtained at different time points; and
processing the comparative measures associated with the different time points to infer a time-dependent host response.

25. The method according to claim 13 wherein steps b) to e) are performed in a disposable cartridge under the control of an automated instrument.

26. The method according to claim 13 wherein the aqueous suspension is heated above at least 70 degrees Celsius.

27. The method according to claim 13 wherein the aqueous suspension is heated above at least 80 degrees Celsius.

28. The method according to claim 13 wherein the aqueous suspension is heated for at least one minute.

29. The method according to claim 13 wherein the aqueous suspension is heated by Joule heating through an electric current applied thereto.

30. The method according to claim 13 wherein the sample is a blood containing sample.

31. The method according to claim 13 wherein the sample is a whole blood sample.

32. The method according to claim 31 wherein the whole blood sample is sampled directly into a blood collection vessel containing the lysis and stabilizing reagent.

33. The method according to claim 32 wherein the blood collection vessel contains less than 10% by weight of Tetradecyltrimethylammonium oxalate in an acidic solution (pH 3.7) of 2-4% Tartaric acid.

34. The method according to claim 13 wherein the complex is separated centrifugally by:
centrifuging the mixture and precipitating the complex, thereby obtaining a precipitated complex;
centrifugally washing the precipitated complex one or more times.

35. The method according to claim 13 wherein the complex is separated by filtration.

36. The method according to claim 31 wherein the complex is separated centrifugally by:
centrifuging the mixture and precipitating the complex, thereby obtaining a precipitated complex;
centrifugally washing the precipitated complex two or more times.

* * * * *